(12) United States Patent
Jarvik

(10) Patent No.: US 9,033,863 B2
(45) Date of Patent: May 19, 2015

(54) SUB-MINIATURE ELECTROMECHANICAL MEDICAL IMPLANTS WITH INTEGRATED HERMETIC FEEDTHROUGHS

(71) Applicant: Robert Jarvik, New York, NY (US)

(72) Inventor: Robert Jarvik, New York, NY (US)

( * ) Notice: Subject to any disclaimer, the term of this patent is extended or adjusted under 35 U.S.C. 154(b) by 0 days.

(21) Appl. No.: 14/047,848

(22) Filed: Oct. 7, 2013

(65) Prior Publication Data

US 2014/0039241 A1 Feb. 6, 2014

Related U.S. Application Data

(62) Division of application No. 12/291,682, filed on Nov. 13, 2008, now Pat. No. 8,550,974.

(51) Int. Cl.
| | |
|---|---|
| *A61N 1/00* | (2006.01) |
| *A61M 1/12* | (2006.01) |
| *A61M 1/10* | (2006.01) |
| *F04D 25/06* | (2006.01) |
| *F04D 29/60* | (2006.01) |
| *H02G 3/22* | (2006.01) |

(52) U.S. Cl.
CPC .............. *A61M 1/127* (2013.01); *A61M 1/101* (2013.01); *F04D 25/06* (2013.01); *F04D 29/605* (2013.01); *H02G 3/22* (2013.01); *A61M 1/122* (2014.02)

(58) Field of Classification Search
None
See application file for complete search history.

(56) References Cited

U.S. PATENT DOCUMENTS

| | | | |
|---|---|---|---|
| 4,516,820 | A | 5/1985 | Kuzma et al. |
| 4,678,868 | A | 7/1987 | Kraska et al. |
| 4,994,078 | A | 2/1991 | Jarvik |
| 5,613,935 | A | 3/1997 | Jarvik |
| 5,759,197 | A | 6/1998 | Sawchuk et al. |
| 5,866,851 | A | 2/1999 | Taylor et al. |
| 5,924,975 | A | 7/1999 | Goldowsky et al. |
| 6,293,901 | B1 | 9/2001 | Prem et al. |
| 6,586,675 | B1 | 7/2003 | Bealka et al. |
| 6,670,074 | B2 | 12/2003 | Spillman et al. |
| 7,357,771 | B2 | 4/2008 | Peters |
| 2002/0102169 | A1 | 8/2002 | Wampler |
| 2004/0046466 | A1 | 3/2004 | Siess et al. |
| 2004/0101746 | A1 | 5/2004 | Ota et al. |
| 2006/0195004 | A1 | 8/2006 | Jarvik |
| 2007/0100196 | A1 | 5/2007 | LaRose et al. |
| 2007/0231135 | A1 | 10/2007 | Wampler et al. |

*Primary Examiner* — Brian T Gedeon
*Assistant Examiner* — Ankit Tejani
(74) *Attorney, Agent, or Firm* — Troutman Sanders LLP

(57) ABSTRACT

Highly miniaturized electro-mechanical medical implants for certain applications cannot be fit into the available anatomic space unless their diameter can be made small enough. With devices such as rotary blood pumps or linear actuators, using rotary or linear electric motors, a thin motor stator that provides sufficient power must be encased in a corrosion resistant hermetically sealed enclosure into which electric wires must pass. Hermetic feedthroughs of the prior art are not structurally suited to maximal miniaturization with optimal electrical properties because of the need for welding of ferrules or other support components. The sub-miniature medical implants having the robust feedthrough of the present invention integrate the feedthrough wires, insulators, and sealing within a radially extending flange that is part of the end wall of the motor enclosure. This permits the largest feedthrough wire and thickest insulator to be built into the limited available space.

12 Claims, 5 Drawing Sheets

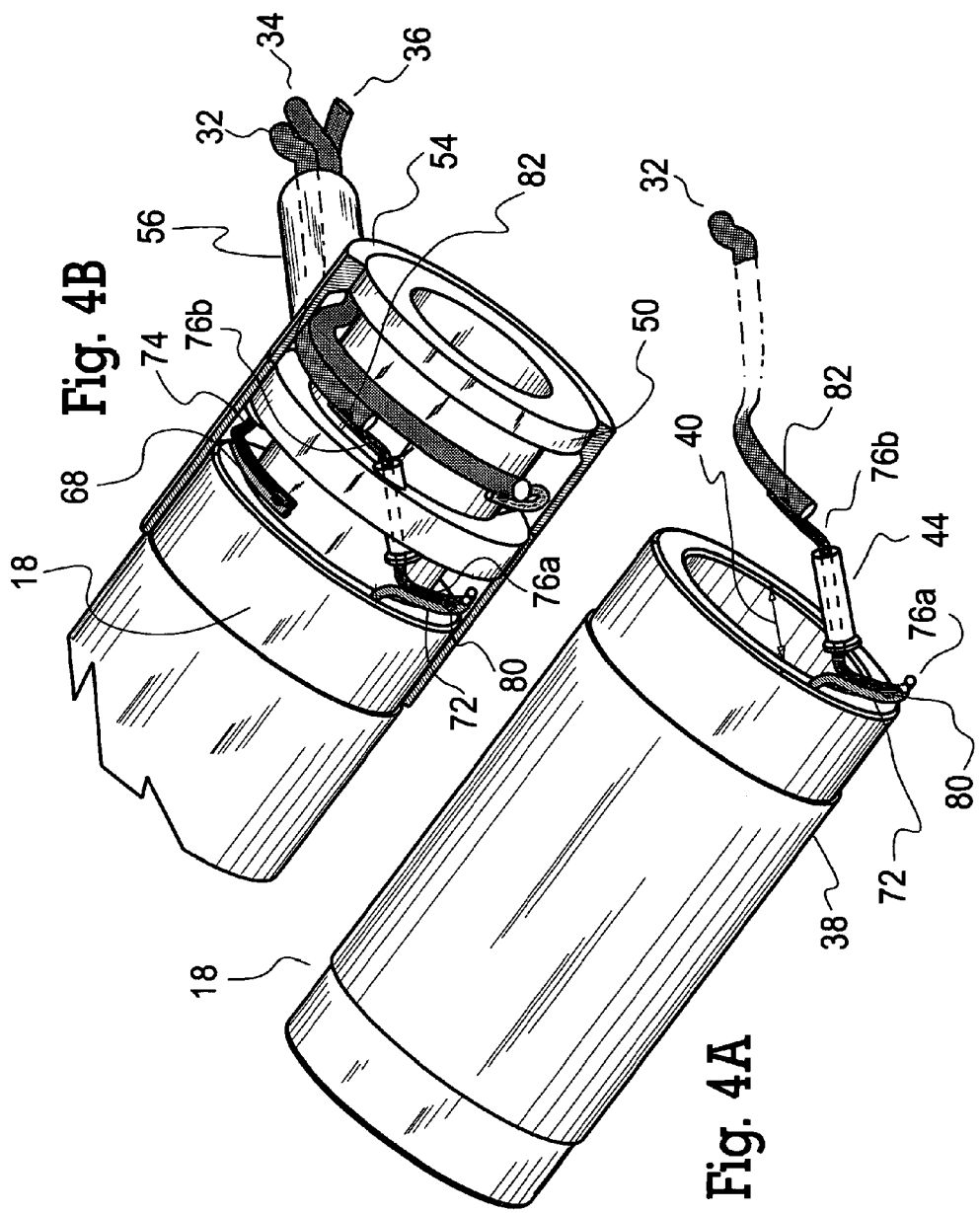

SUB-MINIATURE ELECTROMECHANICAL MEDICAL IMPLANTS WITH INTEGRATED HERMETIC FEEDTHROUGHS

CROSS-REFERENCE TO RELATED APPLICATIONS

This application is a divisional of U.S. application Ser. No. 12/291,682 filed Nov. 13, 2008, which is incorporated herein by reference in its entirety.

GOVERNMENT LICENSE RIGHTS

This invention was made with government support under the Pumps for Kids, Infants, and Neonate (PumpKIN) Preclinical Program, Grant No. HHSN268201000013C, awarded by National Institutes of Health (NIH). The government has certain rights in the invention.

BACKGROUND OF THE INVENTION

Implantable medical devices that utilize electro-mechanical actuators may be used for applications such as blood pumps, mechanically actuated valves, or artificial muscle. Electric motors (Jarvik, Intraventricular Artificial Hearts and Methods of Their Surgical Implantation and Use, U.S. Pat. No. 4,994,078), solenoids (Peters, Heart Assist Devices, Systems and Methods, U.S. Pat. No. 7,357,771) or linear actuators (Goldowski, Linear Pump, U.S. Pat. No. 5,924,975) that are used to power these devices utilize metals such as copper or iron, which are very susceptible to corrosion if exposed to body fluids. Encapsulation, coating, potting, and similar methods that cover the metals with polymer barrier layers may be used for short term implantation in the body, such as days or weeks. But for electromechanical devices that must function for many years, complete exclusion of body fluids by use of hermetically sealed enclosures is required. For decades pacemakers have utilized welded titanium cases to isolate batteries and electronics components, and have brought electrical conductors through the walls of these cases using hermetic feedthroughs having metal to ceramic seals. Examples include Kraska, Hermetic Electrical Feedthrough Assembly, U.S. Pat. No. 4,678,868, and Sawchuk, Protective Feedthrough, U.S. Pat. No. 5,759,197. Many feedthroughs for heart devices and others electronic implants such as cochlear implants or neuro-stimulators have been disclosed in the prior art including designs with multiple contacts such as Taylor, Implantable Medical Device with Multi-Pin Feedthrough, U.S. Pat. No. 5,866,851, or Kuzma, Cochlear Prosthesis Package Connector, U.S. Pat. No. 4,516,820. This has been accomplished using materials such as titanium supports, aluminum oxide insulators, platinium-irridium conductors and pure gold brazing to form a seal between the conductors and the insulators, and between the insulators and the titanium support or other methods such as glass to metal feedthroughs, (Spillman, Glass to Metal Seal, U.S. Pat. No. 6,670,074)

All of these feedthroughs are relatively small components, but in most applications the smallest and most compact geometries are not essential. For example, Wampler shows a multi-pin feedthrough in U.S Patent Application No. 20070231135, entitled Rotary Blood Pump. This device uses three individual feedthroughs located in a recess of a wall of the housing, and is placed in a portion of the centrifugal pump housing near the diffuser, where there is adequate space to weld a ferrule to the housing. LaRose, in U.S. Patent Application No. 20070100196, discloses a very small axial flow blood pump, in which hermetic feedthroughs may be used for the electrical leads, but does not disclose a compact arrangement for the feedthroughs. Rather, LaRose states that the hermetically sealed motor stator enclosure may be welded to a tubular pump housing that passes through it, without providing a structure to compactly provide feedthroughs for the electrical leads. But with very small diameter, generally cylindrical actuators, such as tiny axial blood pumps disclosed by Siess in U.S. Patent Application No. 20040046466, entitled Miniature Motor, or by Jarvik in U.S. Patent Application No. 20060195004, entitled, Minimally Invasive Transvalvular Ventricular Assist Device, the available space to provide power leads may be as little as 2 mm or less. In Siess, no hermetic feedthrough is provided because the device is for short-term application. The present invention provides an extremely compact hermetically sealed feedthrough for tiny electromechanical actuators that integrate the feedthrough structure with the device structure, without the use of a ferrule or the need for welding the feedthrough onto an enclosure containing the stationary motor or solenoid coils.

OBJECTS OF THE INVENTION

1. It is an object of the invention to provide successful miniature blood pumps to support the lives of infants and children.

2. It is an additional object of the invention to provide miniature implantable hermetically sealed electro-mechanical devices such as blood pumps or linear actuators, having the smallest dimensions practical for the necessary forces the devices must apply to tissues of the body.

3. It is a further object of the invention to provide the smallest possible blood pump capable of corrosion free function when implanted for many years.

4. Another object of the invention is to provide a practical and reliable generally cylindrical blood pump that is small enough to be implanted with less invasive surgical techniques, such as robotic thorascopic procedures.

5. An additional object of the present invention is to integrate the structure of hermetic feedthroughs into the motor housing of blood pumps without increasing the diameter of the devices that would be necessary without the use of any feedthroughs at all.

THE DRAWINGS

Figure 3A:
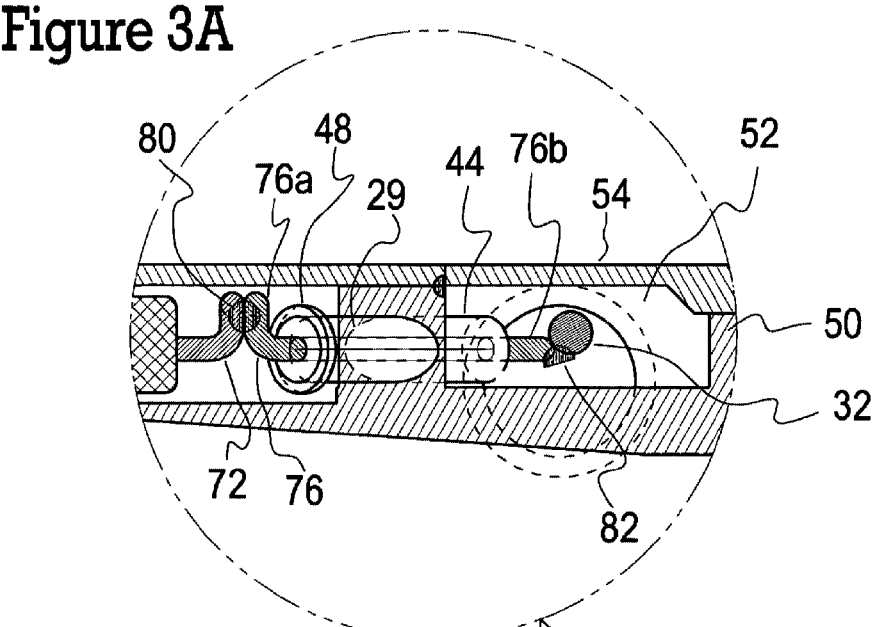
Figure 3B:
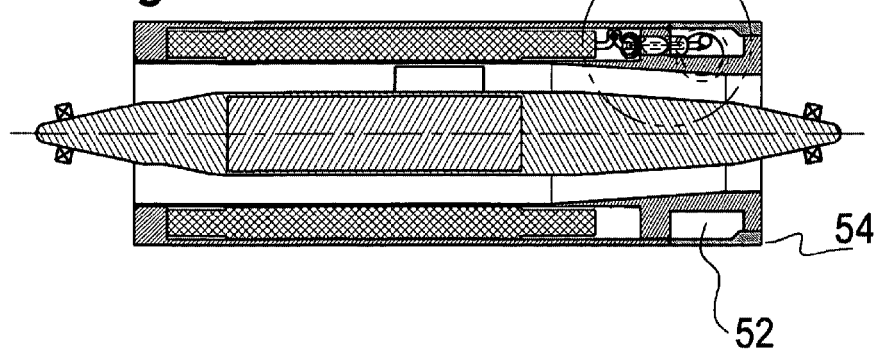
Figure 3C:
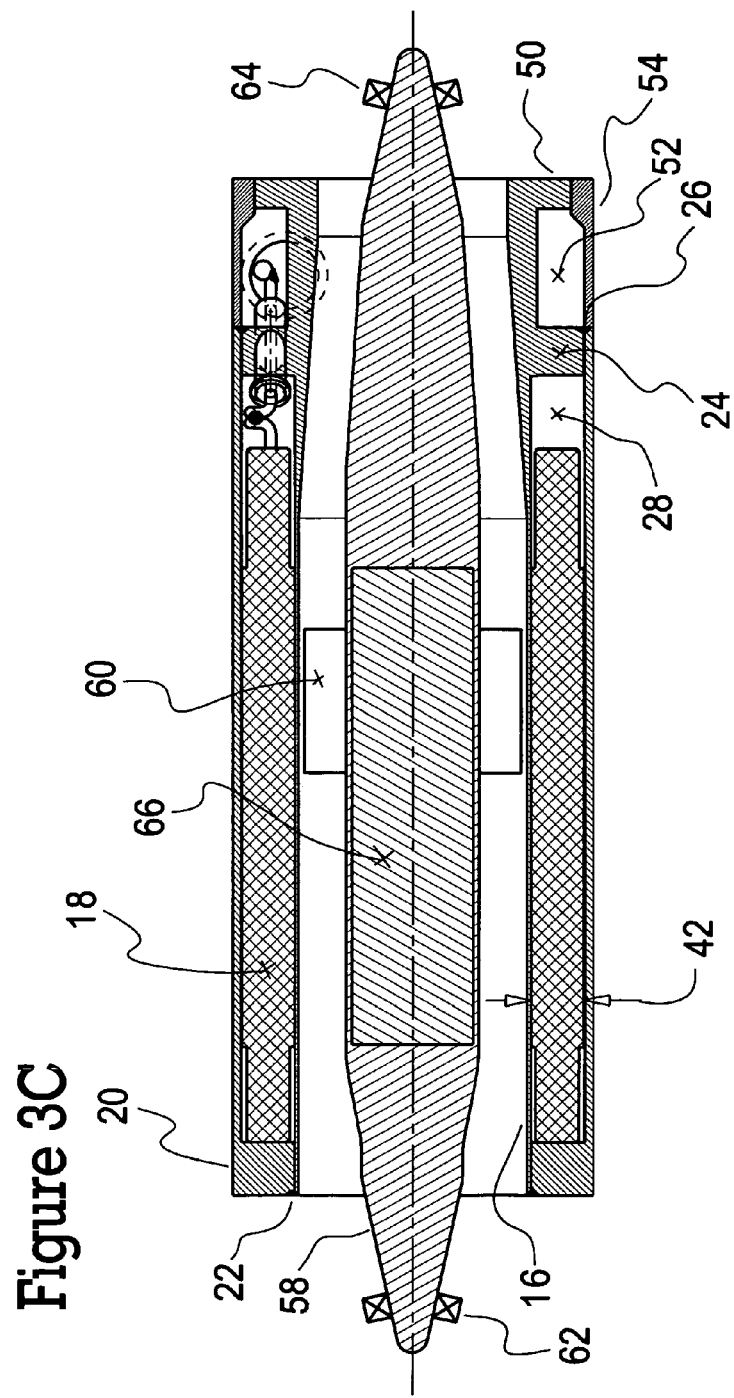

FIG. 3 (includes FIGS. 3A, 3B, and 3C) is a longitudinal section of a blood pump showing the connection of the motor leads and feedthrough wires and the positions of the welds that seal the motor stator within the housing. The magnified view of the feedthrough portion of the blood pump, (FIG. 3A) shows the positions of the wire welds both within the hermetically sealed motor compartment and outside it. FIG. 3B is given to indicate the portion of the Pump magnified in FIG. 3A. FIG. 3C is a larger drawing similar to FIG. 3B, included to make the detail more clearly apparent.

FIG. 4A is a view of the motor stator showing one lead wire, one feedthrough insulator, and an elongated power cable that exits the pump housing: this illustrates the electrical connections of the wires.

FIG. 4B is a partially sectioned cutoff view of the pump housing, sleeve, flange, and feedthrough components showing an arrangement of tangentially wrapped wires both inside the hermetically sealed motor compartment, and on the other side of the flange.

SPECIFIC DESCRIPTION OF THE INVENTION

Figure 1:
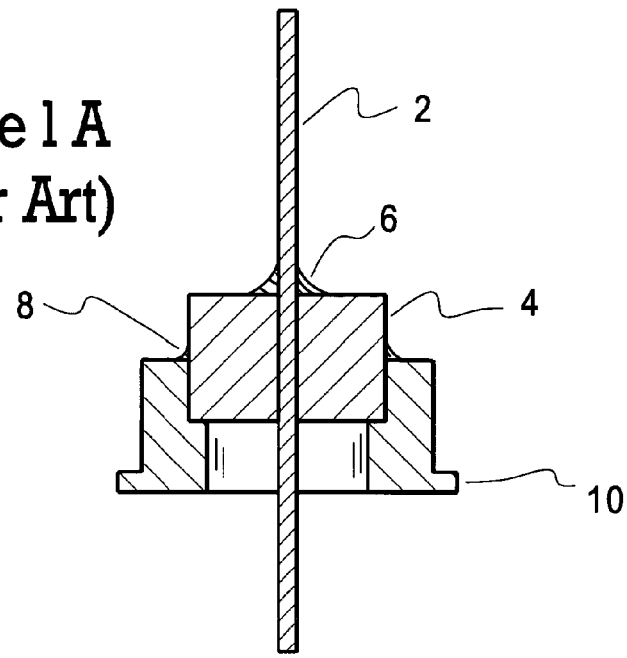
FIG. 1A is a longitudinal section of a prior art feedthrough that uses brazed ceramic to metal components.
FIG. 1B is a longitudinal section of a prior art feedthrough that uses a glass to metal seal.
Figure 1:
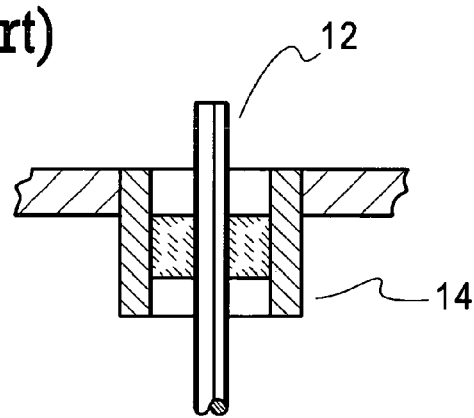

The present invention is adapted to provide a very compact hermetically sealed implantable medical actuator able to be significantly miniaturized. This is accomplished using metal to ceramic brazing or glass to metal types of seals and insulators or similar solid bonded components. FIG. 1A shows an example from the prior art of a ceramic to metal feedthrough that uses a wire 2, brazed into a ceramic insulator 4, with a brazing material such as pure gold 6, 8. The ceramic insulator 4 is in turn brazed into a metal ferrule with a flange 10 that can be welded to the wall of a medical implant such as a pacemaker. FIG. 1B shows a similar feedthrough element, having a wire 12 that is sealed to and insulated from a metal cylinder 14, by fused glass.

In the case of a very small medically implantable actuator there is often a need to maintain the overall diameter of the device as small as possible, for example, in case it is to be inserted into a small diameter blood vessel. There is a limit to how small the wires, ceramic insulators, and components such as ferrules can be made, and space is inevitably lost if a feedthrough sub-assembly needs to be welded onto the wall of a small diameter motor housing. The preferred embodiment of this invention uses a two piece motor housing having a thin walled sleeve 16, best seen in FIG. 2C, that passes through the center of a motor stator 18, shown by itself in FIG. 2B, and best seen together with the motor housing 20, in FIG. 3C. Circumferential welds hermetically join the sleeve to one end of the housing at 22, and also hermetically join the housing to the outer circumference of a flange 24 at weld 26, thus defining an interior motor stator cavity, 28, within which the motor stator 18 is contained. After assembly and welding of the housing components, Flange 24 constitutes one end wall of the motor stator enclosure. Flange 24 is pierced by two or more holes, 29, 30 at the locations where feedthrough wires pass across an end wall of the motor housing. By utilizing hermetically sealed and insulated components that are directly bonded to the flange rather than using a separate ferrule (which would need to be welded to the flange), great space efficiency is obtained. The largest diameter feedthrough wires and thickest ceramic or glass insulators that will fit through the wall of the flange within the radial extent of the motor housing end wall can be used; this provides important strength and durability to the assembly, as well as the best electrical properties (low resistance conductor wire, and high resistance insulator) provided that optimal materials are selected.

An embodiment of a miniaturized implantable blood pump for use with infants and children or for implantation in adults by less invasive endoscopic procedures shown in FIG. 3C incorporates the present invention to permit use of the thinnest motor stator and thus minimize the diameter of the pump. As shown in FIG. 4B, the lead wires 32, 34, 36, may be arranged tangential to the long axis of the pump as shown or they may be arranged to exit the pump substantially in parallel with the long axis of the pump.

For any generally cylindrical rotary or linear motor stator, such as the one shown in FIG. 4A, the outside diameter 38 minus the bore diameter 40 divided by two, represents the thickness of the motor stator components 42 shown as the distance of the cross-hatched motor components between the arrows in FIG. 3C.

In order to provide the largest diameter feedthrough wires and insulators, most of this thickness must be utilized. Therefore, the diameter of the insulator 44 will typically be >50% of the motor stator thickness. Referring to FIG. 3A, hole 29 (shown elongated because it is not formed perpendicular to flange 24, FIG. 3C) accommodates insulator 44 through which a feedthrough wire 76 passes. The insulator has a widened end 48, that prevents it from passing all the way through hole 29 in the flange, when the components are supported in the furnace in the proper orientation during brazing (with the widened end up). In the manufacturing process, the wire may be brazed to insulator first and then the insulator containing the brazed wire may be brazed into the flange. Typically, for a three phase motor, brazing three feedthrough wires and insulators to the flange may be done at the same time, using brazing locations similar to that shown in FIG. 1A. Typical materials that may be used include TiAl6V4 alloy for the pump housing having the flange, alumina for the insulator, platinum-iridium alloy wire for the electrical conductor wire and pure gold for the brazing. The process may be carried out in inert gas at approximately 2,000° F. Alternatively, the feedthrough wires may be affixed across the holes in flange 24 using glass to metal bonding technology such as illustrated in FIG. 1B. If this is done special fixturing may be used to hold the wires centered in the holes in said flange without contacting it when the glassy insulating material melts and fuses with the wire and the housing flange.

The blood pump incorporating the present invention, shown in FIG. 3C, includes the motor housing 20, housing sleeve component 16, which is made integral with the flange 24. This sleeve component also includes a second flange 50 and thus a groove 52 exists between the two flanges. This groove contains the feedthrough wires as they emerge from the motor compartment 28, through the insulators. The external lead wires, that conduct electric power to the motor from the battery or wall power source, are electrically connected to the feedthrough wires within groove 52, by usual methods such as welding, soldering or crimping. After the wires are attached and insulated, the groove containing them may be encapsulated or potted with a durable insulating material such as epoxy in the manner that some pacemaker headers encapsulate feedthrough wires in epoxy. A cover, 54, which may be formed as two pieces, may be provided to further protect the wires, and conduit 56 per FIG. 4B, designed to provide support for exit of the wires and attachment of a strain relief (not shown) may be formed integral with the cover.

Reviewing the structures shown in FIG. 3C described above, we have disclosed an elongated, generally cylindrical motor enclosure which confines the motor within a hermetically sealed cavity when two circumferential welds are made. The enclosure includes a flange with two or more feedthroughs located on one end, or if required, on both ends.

Within the center of the motor bore the motor rotor 58, which carries the impeller 60 of a hydrodynamic pump, such as a mixed flow pump or an axial flow pump, is supported for rotation by bearings, schematically illustrated at 62, 64. These may be blood immersed bearings, supported by posts (not shown) extending inward from the motor housing assembly, or the rotor may be supported magnetically, or by a combination of magnetic and hydrodynamic forces, or by mechanical bearing members at the tips of the pumping blades, etc. Any type of rotor bearings may be used. When power is appropriately applied to the various motor windings within the motor stator, magnetic forces are applied to the rotor magnet 66, causing it to turn.

Figure 2A:
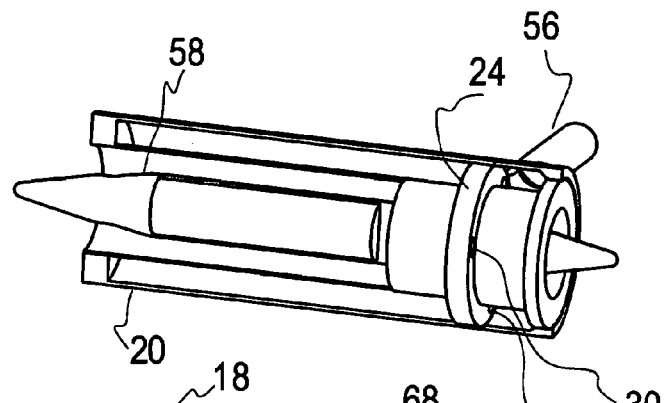
FIG. 2A is a partially cutaway drawing of a blood pump showing the motor housing and other components without the motor stator and feedthrough wires.
Figure 2B:
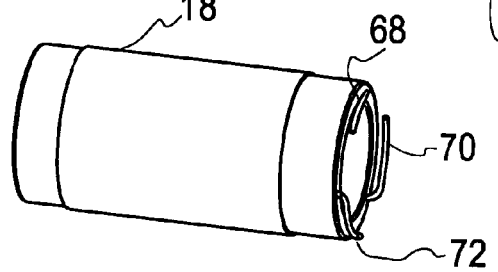
FIG. 2B is a drawing of the motor stator of the blood pump partially shown in FIG. 2A, showing three motor lead wires emerging at the face of the stator, with each of the three wires wrapped tangentially.
Figure 2C:
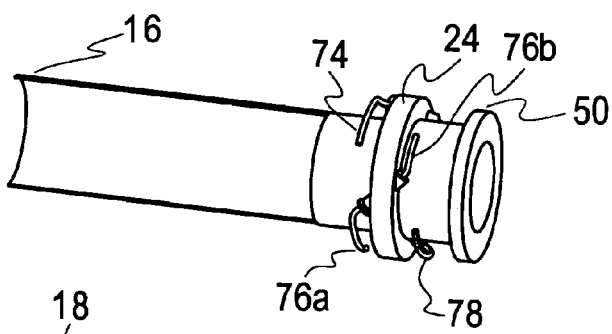
FIG. 2C is a view of the inner sleeve of the pump showing a flange and feedthrough wires passing through insulators supported by the flange to connect the three motor leads to the electrical system and power cables that provide power and control of the motor.
Figure 2D:
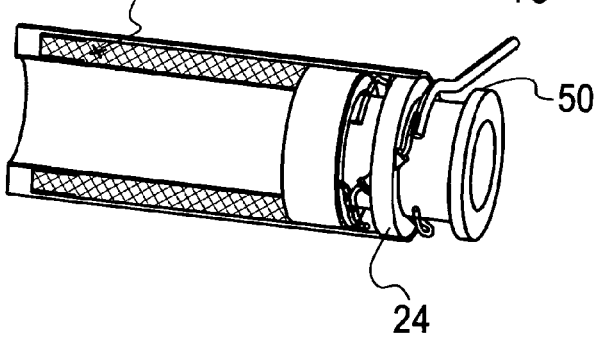
FIG. 2D is a partially cutaway view of the motor stator (shown partially crosshatched) assembled within a compartment formed between the sleeve and housing components, and also showing the motor leads connected to the feedthrough wires.

FIG. 2B-FIG. 2D illustrates the assembly of the blood pump motor into the housing and the connections of the feedthrough wires to the motor wires and the external lead wires. In the case of a three phase brushless DC motor only three wires are necessary. To best match the position of three equally spaced feedthroughs, the motor wires 68, 70, 72 exit the end of the motor stator at 120° angular separation and may be wrapped in a generally tangential position as shown in FIG. 2B. As best seen in FIG. 2C the motor housing sleeve 16 has flange 24, with three feedthroughs already formed, after removal from the furnace. Feedthrough wires 74, 76 and 78 are spaced 120° apart and can be rotationally lined up with the motor wires. Each of the feedthrough wires has one end on the side of flange 24 that will be inside the motor enclosure 28 per FIG. 3C and one end on the other side of the flange. This is clearly seen for wire 76, that has one end 76a inside the motor enclosure and the other end 76b, outside the motor enclosure.

Referring to FIG. 2B-D it can be seen that the motor stator may be placed over the sleeve, the motor wires may be connected to the feedthrough wires and insulated, such as by welding as illustrated in FIG. 3A at 80, and then covering them with shrink fit tubing, and then the motor housing can be placed over the motor stator and circumferentially welded together at positions 22 and 26 per FIG. 3C, as previously described.

FIGS. 4A and 4B most clearly show the feedthrough structures. FIG. 4A, which omits the motor enclosure sleeve, flange, and housing for clarity, shows the motor stator 38, one motor wire 72 and one feedthrough wire 76a welded to it at weld 80. The feedthrough wire passes through the center of one insulator 44 and they are brazed or otherwise hermetically sealed together. The other part of this feedthrough 76b is welded to one of the external motor leads, 32 at weld 82. FIG. 4B, includes the motor stator 18, sleeve 16, flange 24, motor housing 20, and wire cover with conduit 56. The arrangement in which three motor wires are connected to three feedthrough wires within the motor enclosure, and are in turn connected to three external motor leads within the groove formed between flange 24 and flange 50 is clearly apparent, although not all of each of the three feedthroughs and sets of wires is visible in the cut-away view.

It is also apparent to one skilled in the art that an embodiment of the present invention could be constructed in which the feedthroughs were mounted to a flange (or end wall) extending inwardly from the outer wall of the motor housing, rather than to a flange extending outwardly from a sleeve as shown in the drawings. This additional configuration would make connection of the motor wires to the feedthrough wires more difficult, since the connection would need to be made inside the bore, but nonetheless, this could be accomplished and the resulting device would function properly.

Thus it is clear that the invention disclosed provides thin walled electromechanical actuators for medical implants that incorporate an effective space efficient integrated hermetic feedthrough. One type of device disclosed is a highly miniaturized small diameter implantable blood pump.

The information disclosed in the description of the present invention is intended to be representative of the principles I have described. It will thus be seen that the objects of the invention set forth above and those made apparent from the preceding description are efficiently obtained and that certain changes may be made in the above articles and constructions without departing from the scope of the invention. It is intended that all matter contained in the above description and shown in the accompanying drawings shall be interpreted as illustrative but not in a limiting sense. It is also understood that the following claims are intended to cover all of the generic and specific features of the invention herein described and all statements of the scope of the invention which, as a matter of language, might be said to fall there between.

I claim:

1. An implantable blood pump comprising;
   a. A slot-less brushless DC motor having a motor stator enclosed in a welded hermetically sealed housing,
   b. A cylindrical bore through said housing within which a hydrodynamic pump rotor and impeller rotate on bearings,
   c. Three electric feedthroughs adapted to conduct electric power to terminations of said motor stator, circumferentially spaced apart from one another at locations on one end of said housing, individually hermetically sealed, insulated, and formed integral with one end wall of said housing, and
   d. the three hermetically sealed feedthroughs are enclosed within the housing.

2. The blood pump of claim 1 having a circumferential groove outside and adjacent to one end of the hermetically sealed housing within which groove connections of motor power leads to the electric feedthroughs may be made and encapsulated in an insulating material such as epoxy.

3. A miniaturized implantable medical device having a hermetically sealed corrosion resistant enclosure to contain the stator of an electro-magnetic actuator, comprising:
   a. a first generally cylindrical housing member having an outer generally tubular wall adapted to receive said motor stator within said tubular wall, and a washer shaped end wall confining the motor stator on one end,
   b. A second generally cylindrical housing member having a thin-walled sleeve adapted to fit through a bore of said motor stator and contact the hole within the washer shaped end wall of said first housing member around its entire circumference,
   c. Said second housing member including a flange extending outwardly from said sleeve to enclose said motor stator and make circumferential contact with said housing, said flange having two or more hermetic feedthroughs, comprised of wires passing through the flange, insulated by suitable material hermetically bonded to the inside of holes passing through the flange and also hermetically bonded to wires passing through holes in the insulating material,
   d. Said first and second housing members welded circumferentially at each end to hermetically seal the motor stator therewithin, and
   e. Said two or more hermetic feedthroughs and said wires passing through the flange are enclosed within the outer tubular wall.

4. The feedthrough of claim 3 in which the medical device is an implantable rotary blood pump.

5. The feedthrough of claim 3 in which each electric wire passes through a separate hole in said end wall within which it is sealed and insulated by a surrounding glass or ceramic ring, and the diameter of said hole in the flange is greater than one half of the radial dimension of the motor stator contained within said enclosure.

6. The feedthrough of claim 3 in which said hermetically sealed enclosure contains a slot-less brushless DC motor stator.

7. The feedthrough of claim 3 in which three electrical wires are located around the circumference of the end wall at approximately 90-180 degrees of separation, and the motor stator of the electro-magnetic actuator includes three phase brushless DC motor winding with terminations spaced circumferentially at positions aligned with the wires.

8. A hermetically sealed corrosion resistant enclosure to contain the stator of a miniaturized implantable medical device comprising:
   a. a first generally cylindrical housing member having an outer generally tubular wall adapted to receive said motor stator within said tubular wall, and a washer shaped end wall confining the motor stator on one end,
   b. A second generally cylindrical housing member having a thin-walled sleeve adapted to fit through a bore of said motor stator and contact the hole within the washer shaped end wall of said first housing member around its entire circumference,
   c. Said second housing member including a flange extending outwardly from said sleeve to enclose said motor stator and make circumferential contact with said housing,
   d. said washer shaped end wall of said first housing member having two or more hermetic feedthroughs, comprised of wires passing through the end wall, insulated by suitable material hermetically bonded to the inside of holes passing through the end wall and also hermetically bonded to wires passing through holes in the insulating material,
   e. Said first and second housing members welded circumferentially at each end to hermetically seal the motor stator therewithin, and
   e. Said two or more hermetic feedthroughs and said wires passing through the end wall are enclosed within the outer tubular wall.

9. The feedthrough of claim 8 in which the medical device is an implantable rotary blood pump.

10. The feedthrough of claim 8 in which each electric wire passes through a separate hole in said end wall within which it is sealed and insulated by a surrounding glass or ceramic ring, and the diameter of said hole in the flange is greater than one half of the radial dimension of the motor stator contained within said enclosure.

11. The feedthrough of claim 8 in which said hermetically sealed enclosure contains a slot less brushless DC motor stator.

12. The feedthrough of claim 8 in which three electrical wires are located around the circumference of the end wall at approximately 90-180 degrees of separation, and the motor stator of the electro-magnetic actuator includes three phase brushless DC motor winding with terminations spaced circumferentially at positions aligned with the feedthrough wires.

* * * * *